United States Patent [19]
Venkateshwaran et al.

[11] Patent Number: 5,952,000
[45] Date of Patent: Sep. 14, 1999

[54] FATTY ACID ESTERS OF LACTIC ACID SALTS AS PERMEATION ENHANCERS

[75] Inventors: Srinivasan Venkateshwaran; David Fikstad, both of Salt Lake City; Sonal R. Patel, Sandy, all of Utah

[73] Assignee: TheraTech, Inc., Salt Lake City, Utah

[21] Appl. No.: 08/959,946

[22] Filed: Oct. 29, 1997

Related U.S. Application Data

[63] Continuation-in-part of application No. 08/741,071, Oct. 30, 1996, abandoned.

[51] Int. Cl.$^6$ ................................................ A61F 13/02
[52] U.S. Cl. ........................... 424/448; 514/946; 514/947
[58] Field of Search ............................ 424/448; 514/946, 514/947

[56] References Cited

U.S. PATENT DOCUMENTS

| | | |
|---|---|---|
| 3,472,931 | 10/1969 | Stoughton . |
| 3,551,154 | 12/1970 | Di Blas et al. . |
| 3,728,447 | 4/1973 | Osipow et al. . |
| 3,742,951 | 7/1973 | Zaffaroni . |
| 3,797,494 | 3/1974 | Zaffaroni . |
| 4,006,218 | 2/1977 | Sipos . |
| 4,164,190 | 8/1979 | Newman . |
| 4,198,311 | 4/1980 | France et al. . |
| 4,422,952 | 12/1983 | Koulbanis et al. . |
| 4,568,343 | 2/1986 | Leeper et al. . |
| 4,761,279 | 8/1988 | Khalil et al. . |
| 4,820,720 | 4/1989 | Sander et al. . |
| 4,822,601 | 4/1989 | Goode et al. . |
| 4,849,224 | 7/1989 | Chang et al. . |
| 4,855,294 | 8/1989 | Patel et al. . |
| 4,863,970 | 9/1989 | Patel et al. . |
| 4,888,354 | 12/1989 | Chang et al. . |
| 4,940,586 | 7/1990 | Cheng et al. . |
| 4,960,814 | 10/1990 | Wu et al. . |
| 4,973,468 | 11/1990 | Chiang et al. . |
| 4,983,395 | 1/1991 | Chang et al. . |
| 5,006,342 | 4/1991 | Cleary et al. . |
| 5,093,112 | 3/1992 | Birtwistle et al. . |
| 5,122,383 | 6/1992 | Heiber et al. . |
| 5,152,997 | 10/1992 | Ebert et al. . |
| 5,154,122 | 10/1992 | Goldschmidt . |
| 5,212,199 | 5/1993 | Heiber et al. . |
| 5,227,169 | 7/1993 | Heiber et al. . |
| 5,302,395 | 4/1994 | Ebert et al. . |
| 5,314,694 | 5/1994 | Gale . |
| 5,427,772 | 6/1995 | Hagan . |

FOREIGN PATENT DOCUMENTS

| | | |
|---|---|---|
| 96/02903 | 2/1996 | WIPO . |
| 96/37231 | 11/1996 | WIPO . |

OTHER PUBLICATIONS

Dohi et al., Enhancing Effects of Myristyl Lactate and Lauryl Lactate Percutaneous Absorption of Indomethacin, *Pharm. Bull.* 2877–2897 (1990).

Kaiho et al., Enhancing Effect of Letyl Lactate on the Percutaneous Absorption in Rats. *Chem. Pharm. Bull.* 37(4) 1114–1116 (1989).

Murphy et al. *Acyl Lactylates in Cosmetics*, 1978.

Murphy et al. Sorption of Acyl Lactylates by Hair and Skin as Documented by Ratio Tracer Studies, *Toiletries* 43–49 (1979).

Osipow et al., Fatty Acid Lactylates, *D&CL.* Mar. & May, 1969.

*Primary Examiner*—D. Gabrielle Brouillette
*Attorney, Agent, or Firm*—Thorpe, North & Western, L.L.P.

[57] ABSTRACT

A transdermal drug delivery system which enhances the delivery of the drug comprises a composition containing, as an enhancer, one or more $C_6$ to $C_{22}$ fatty acid esters of a lactic acid salt. These compositions are made up of a safe and effective amount of an active pharmaceutical permeant contained in a penetration-enhancing vehicle comprising, 0.25 to 50% w. of the fatty acid ester of a lactic acid salt enhancer in a suitable pressure sensitive adhesive carrier vehicle formed from and aqueous emulsion based pressure sensitive adhesive.

20 Claims, No Drawings

FATTY ACID ESTERS OF LACTIC ACID SALTS AS PERMEATION ENHANCERS

This application is a continuation-in-part of application Ser. No. 08/741,071 filed Oct. 30, 1996, now abandoned.

FIELD OF THE INVENTION

The present invention relates to the use of fatty acid esters of lactic acid salts as permeation enhancers in matrix patch delivery devices. More particularly, this invention relates to the use of esters of one or more fatty acids and lactic acid salts as permeation enhancers when formulated with aqueous emulsion based pressure sensitive adhesives resulting in the formation of matrix patch devices for the transdermal delivery of a wide range of active permeants.

BACKGROUND OF THE INVENTION AND DESCRIPTION OF PRIOR ART

The transdermal administration of drugs is becoming increasingly accepted as a preferred mode of delivery.

Transdermal delivery of drugs provides many advantages over conventional oral administration. Advantages of transdermal systems include convenience, noninterrupted therapy, improved patient compliance, reversibility of treatment (by removal of the system from the skin), elimination of "hepatic first pass" effect, the high degree of control over blood concentration of any particular drug and consequent reduction of side effects.

Although transdermal systems have many advantages, most drugs are not amenable to this mode of administration due to the well known barrier properties of the skin. Molecules moving from the environment into and through intact skin must first penetrate the stratum corneum and any material on its surface. The molecule must then penetrate the viable epidermis, the papillary dermis, and then the capillary walls and into systemic circulation. Along the way, each of the above mentioned tissues will exhibit a different resistance to penetration by the same molecule. However, it is the stratum corneum that presents the greatest barrier to absorption of topical compositions or transdermally administered drugs. The stratum corneum, the outer horny layer of the skin, is a complex structure of compact keratinized cell remnants separated by lipid domains. Compared to the oral or gastric mucosa, the stratum corneum is much less permeable to outside molecules.

The flux of a drug across the skin can be increased by changing either a) the resistance (the diffusion coefficient), or b) the driving force (the solubility of the drug in the stratum corneum and consequently the gradient for diffusion). Many enhancer compositions have been developed to change one or more of these factors, and are known in the art. U.S. Pat. Nos. 4,006,218, 3,551,154 and 3,472,931, for example, respectively describe the use of dimethylsulfoxide (DMSO), dimethyl formamide (DMF) and N,N-dimethylacetamide (DMA) to enhance the absorption of topically applied drugs through the stratum corneum. Combinations of enhancers consisting of diethylene glycol monoethyl or monomethyl ether with propylene glycol monolaurate and methyl laurate are disclosed in U.S. Pat. No. 4,973,468 as enhancing the transdermal delivery of steroids such as progestogens and estrogens. A dual enhancer consisting of glycerol monolaurate and ethanol for the transdermal delivery of drugs is shown in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 shows penetration-enhancing compositions for topical application comprising an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

The use of sorbitan esters of long chain aliphatic acids as skin permeation enhancers is disclosed in U.S. Pat. Nos. 5,122,383; 5,212,199 and 5,227,169. Skin permeation enhancement using aliphatic alcohol esters of lactic acid is disclosed in U.S. Pat. No. 5,154,122, World Patent 95/09006 and in Dohi et al., Enhancing Effects of Myristyl Lactate and Lauryl Lactate on Percutaneous Absorption of Indomethacin, Chem Pharm. Bull. 38 (October 1990) 2877–2879. U.S. Pat. No. 5,314,694 also makes reference to the use of esters of fatty acid alcohols, i.e. lauryl alcohol and lactic acid as a permeation enhancer component.

World Patent 96/37231 teaches the use of acyl lactylates as permeation enhancers for drug delivery purposes. This patent is specific to esters of fatty acids and lactic acid such as caproyl lactylic acid and lauroyl lactylic acid. It is stated that the salt form of acyl lactylates are not effective as permeation enhancers.

Skin permeation enhancement due to fatty acid sucrose esters is disclosed in U.S. Pat. No. 4,940,586. Penetration enhancement resulting from combining free base and acid addition salt combinations of drugs is taught in U.S. Pat. No. 4,888,354. Enhancement of drugs by means of subsaturation in a carrier is disclosed in U.S. Pat. No. 5,164,190.

Occlusive adhesive devices, i.e. patches, for transdermal delivery of drugs is taught in U.S. Pat. Nos. 4,849,224; 4,983,395; 5,152,997 and 5,302,395. These patches are in reservoir or matrix forms as will be more fully characterized in the detailed description below.

Many of the enhancer systems possess negative side effects such as toxicity, skin irritation and incompatibility with the drugs or other ingredients making up the transdermal system.

U.S. Pat. No. 4,855,294 discloses compositions for reducing skin irritation caused by drug/enhancer compositions having skin irritation properties comprising a percutaneously absorbable drug, a binary enhancer composition consisting of a solvent and a cell envelope disordering compound, combined with an amount of glycerin sufficient to provide an anti-irritating effect.

It would be desirable to have an enhancer composition which not only enabled the passage of drug compositions across the skin barrier but which was also beneficial to the moisturization, stability and overall vitality of the epidermis. Skin having properly moisturized stratum corneum is smooth to the touch, flexible and elastic due to the presence of sufficient bound water. A 1% variation of water content may be enough to modify skin elasticity and permeability.

Suitable skin hydration also promotes transdermal delivery of drugs through the stratum corneum.

Fatty acid lactylates and glycolates are known to be used as hair conditioners as shown by U.S. Pat. No. 3,728,447. Further, fatty acid lactylates and their salts, prepared from $C_6$ to $C_{22}$ fatty acids, are known to be used in cosmetics and have the ability to complex with skin proteins. See Murphy, et al., Acyl Lactylates in Cosmetics, D&CI (May, 1978) 35 ff and Murphy, et al., Sorption of acyl lactylates by hair and skin as documented by radio tracer studies, Cosmetics & Toiletries, 94 (March 1979) 43–49. Combinations of acyl lactylates or glycolates with soaps or synthetic detergents in skin conditioning toilet bars is the subject of U.S. Pat. No. 4,198,311. The use of a salt of a fatty acid ester of lactylic acid as one of many components in a shaving cream formulation is taught in U.S. Pat. No. 4,761,279.

Lanolinyl lactylates, are shown in U.S. Pat. No. 4,422,952 to be used in water-in-oil emulsions as cosmetic supports or pharmaceutical excipients, e.g. to be used in ointments, balms, creams and the like. No physiological effect is attributed to these esters.

U.S. Pat. No. 4,822,601 is drawn to cosmetic base compositions exhibiting therapeutic properties including sucrose fatty acid esters and fatty acid lactylates, with or without shea butter. Following application to the skin, a thickening of the epidermal layer was noted indicating a healthier and less dry skin. It was noted that topical application of such compositions also demonstrated enhanced wound healing properties and decreased sensitivity to UV light.

Extensive summaries of the prior art for acyl lactylates and of the properties of such for cosmetic use are found in U.S. Pat. No. 5,427,772 and World Patent 96/37231.

In none of the above is the use of fatty esters of lactic acid salts as permeation enhancers combined with pressure sensitive adhesives (PSA) to form matrix devices for active pharmaceutical agents taught, suggested or demonstrated.

OBJECTS AND BRIEF SUMMARY OF THE INVENTION

Accordingly, it is an object of the present invention to provide a composition for enhancing the transdermal delivery of drugs which has good skin tolerability and presents minimal risks of skin toxicity or irritation.

It is still another object of the invention to provide a composition for the transdermal administration of drugs containing, as an enhancer, one or more $C_6$ to $C_{22}$ fatty acid esters of lactic acid salts, combined with an emulsion based pressure sensitive adhesive.

Another object of the invention is to provide a method of enhancing the transdermal delivery of a variety of drugs having either or both hydrophobic and hydrophilic characteristics using one or more $C_6$ to $C_{22}$ fatty acid esters of lactic acid salts as an enhancer when combined with aqueous emulsion based pressure sensitive adhesives.

These and other objects may be realized by means of a composition for transdermal delivery consisting of a broad category of pharmaceutically-active agents which are lipophilic or hydrophilic, including salts, and which produce minimal or no skin irritation to human or animal tissue systems. The invention provides penetrating transdermal compositions based on the use of a pharmaceutically-active agent dissolved in, or admixed with, a penetration-enhancing amount of one or more $C_6$ to $C_{22}$ fatty acid ester of a lactic acid salt as more fully described below, in a suitable aqueous emulsion based pressure sensitive carrier vehicle. Suitable pressure sensitive adhesives will be subsequently described.

The drug, enhancer, pressure sensitive adhesive combination is contained in an occlusive device for purposes of holding the composition against the skin or mucosa surface for administration. Such devices are generally patches for adhesion to the skin surface in matrix form.

The invention is therefore not limited to any specific category or categories of permeants, but is inclusive of all therapeutically active compounds, and their uses to which they are responsive as more fully set forth herein. The invention is also inclusive of mixtures of permeants which may be administered simultaneously.

Also, the invention is drawn to treatment methods by means of which an effective amount of a permeant, combined with the enhancer system and pressure sensitive adhesive, is applied to the skin of a human or animal subject.

The combination of permeant, fatty acid esters of lactic acid salts and pressure sensitive adhesive in a delivery system is preferably limited to a delivery patch in matrix form. Such patches will contain an occlusive backing.

DETAILED DESCRIPTION OF THE PREFERRED EMBODIMENTS

The following definitions will be useful in describing the invention and will eliminate the need for repetitive explanations.

When used in context, the terms "enhancement", "penetration enhancement" or "permeation enhancement" relates to an increase in the permeability of the skin to a drug, so as to increase the rate at which the drug permeates through the skin. The enhanced permeation effected through the use of such enhancers can be observed, for example, by measuring the rate of diffusion of the drug through animal or human skin using a diffusion cell apparatus. The diffusion cell is described by Merritt et al. Diffusion Apparatus for Skin Penetration, *J. of Controlled Release*, 1 (1984) pp. 161–162.

By "transdermal" delivery, is meant transdermal or percutaneous administration, i.e., delivery by passage of drug through the skin. Hence the terms "skin", "derma", "epidermis", and the like shall also be used interchangeably unless specifically stated otherwise.

By "application situs" is meant a site suitable for topical application with or without the means of a mechanical sustained release device, patch or dressing, e.g., behind the ear, on the arm, back chest, stomach, leg, top of foot, etc.

By the term "permeant" or "drug" is meant any chemical material or compound suitable for transdermal administration which includes a desired biological or pharmacological effect by application to the "application situs" for systemic delivery.

Such substances include the broad classes of compounds normally delivered through body surfaces such as the skin. In general, this includes therapeutic agents in all of the major therapeutic areas including, but not limited to, antiinfectives such as antibiotics and antiviral agents, analgesics and analgesic combinations, anorexics, antidiarrheal, antihistamines, anti-inflammatory agents, antimigraine preparations, antimotion sickness agents, antinauseants, antineoplastic, antiparkinsonism drugs, antipruritic, antipsychotic, antipyretics, antispasmodics including gastrointestinal and urinary, anticholinergic, sympathomimetic, xanthine derivatives, cardiovascular preparations including calcium channel blockers, beta-blockers, antiarrythmics, antihypertensives, diuretics, vasodilator including general coronary, peripheral and cerebral, central nervous system stimulants including cough and cold preparations, decongestants, diagnostics, hormones, immunosupressives, muscle relaxants, parasympatholytic, parasympathomimetic, psychostimulants, sedatives and tranquilizers. The term "permeant" is also meant to include mixtures. By mixtures is meant combinations of permeants from different categories, mixtures of permeants from the same category and mixtures of free base and salt forms of the same or different permeants from the same or different categories.

By "effective" amount of a drug or permeant is meant a nontoxic but sufficient amount of a compound to provide the desired systemic effect. An "effective" amount of permeation enhancer as used herein means an amount selected so as to provide the desired increase in transdermal permeability and, correspondingly, the desired depth of penetration, rate of administration and amount of drug. By "effective" amount of fatty acid ester of glycolic acid or it salts or any other enhancer or carrier component is meant the amount found beneficial in a particular delivery system to achieve the desired delivery of the drug from the system.

By "drug delivery system", "drug/enhancer composition" or any similar terminology is meant a formulated composition containing the drug to be transdermally delivered in combination with such "carriers" or "vehicles", penetration enhancers, excipients, or any other additives.

By the term "matrix", "matrix patch" or "matrix system" is meant an active permeant homogeneously combined in a biocompatible pressure sensitive adhesive which may or may not also contain other ingredients or in which the enhancer is also homogeneously dissolved or suspended. A matrix system is usually an occlusive adhesive patch having an impermeable film backing and, before transdermal application, a release liner on the surface of the adhesive opposite the film backing. A matrix system therefore is a unit dosage form of a drug composition in an adhesive carrier, also containing the enhancer and other components which are formulated for maintaining the drug composition in the adhesive in a drug transferring relationship with the derma or skin. Adhesive patches having non-occlusive backings are also considered to be within the scope of this definition unless specifically excluded.

The compositions of this invention require, at a minimum, a permeant capable of producing systemic effects in a carrier vehicle containing, as an enhancer, a fatty acid ester of a lactic acid salt. Such carrier vehicle is a pressure sensitive adhesive obtained from an aqueous based emulsion. In addition, the fatty acid esters of a lactic acid salt may be combined with other enhancers, such as cell envelope disordering compounds.

Cell envelope disordering compounds are known in the art as being useful in topical pharmaceutical preparations. These compounds are thought to assist in skin penetration by disordering the lipid structure of the stratum corneum cell-envelopes. A representative listing of these compounds is described in the patents cited in the prior art section above which are incorporated herein by reference.

Lactic acid salts that are useful the preparation of esters are those represented by the formula:

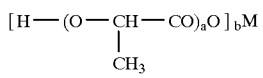

where a is an integer of 1 to 4, b is 1 or 2 and M is a pharmaceutically acceptable salt forming counterion having a valency of 1 or 2. For example, alkali, alkaline earth, ammonium and amine salts are suitable counterions. Representative of these are alkali metal salts such as sodium and potassium; alkaline earth metal salts such as magnesium and calcium and ammonium and amine salts. The amines may be primary, secondary or tertiary and may be alkyl, aryl, alkaryl and aralkyl amines. By alkyl and alkenyl is meant any straight or branched, saturated or unsaturated, chain having from 1 to 22 carbon atoms and by aryl is meant any carbocyclic or heterocyclic group having properties of aromaticity. By aralkyl and alkaryl is meant any combination of alkyl and aryl.

Fatty acids used in the preparation of esters are those represented by the formula RCOOH, where R is a $C_5$ to $C_{21}$ alkyl or alkenyl chain which may be either straight or branched chained and which may contain hydroxy substituents. Straight $C_8$ to $C_{18}$ alkyl, alkenyl or hydroxy substituted alkyl or alkenyl chains are preferred. Representative of saturated acids, where R is alkyl, are caproic acid, caprylic acid, capric acid, lauric acid, myristic acid, palmitic acid, stearic acid, and the like. Representative of unsaturated acids, where R is alkenyl, are palmitoleic acid, oleic acid, linoleic acid, linolenic acid, ricinoleic acid, arachidonic acid and the like. Mixtures of acids, including mixtures of saturated and unsaturated acids may also be used.

The fatty acid esters of lactic acid salts may be represented by the formula:

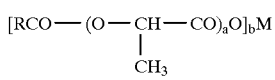

where R, M, a and b are as represented above. Preferably M is a salt forming counterion selected from the group consisting of Na, K, Ca, Mg and ammonium or amines salts. Since these fatty acid esters of lactic acid salts are described in the prior art, further definition is not necessary. These compounds, sometimes also described as acyl lactylate salts are available from R.I.T.A. Corporation (Woodstock, Ill.) under the Pationic trade name. Some members of this class of compounds are commonly used in the food industry for their effect on bread dough properties, and other members have been used in cosmetics as emulsifiers, hair conditioners, and skin moisturizers.

Particularly preferred fatty acid esters of lactic acid salts are members selected from the group consisting of sodium lauroyl lactylate, potassium lauroyl lactylate, sodium caproyl lactylate, sodium cocoyl lactylate, tromethamine lauroyl lactylate and the like.

The fatty acid esters of lactic acid salts when used as enhancers, may be present in an enhancer/carrier system in amounts ranging from between about 0.25 to 50% w. The effective amount of enhancer may vary depending on any number of factors such as the hydrophilic/hydrophobic properties of the drug, drug concentration, etc. In all systems ranges of between about 0.25 and 30% w are preferable. Most preferably the enhancer content will range between about 0.5 to 15% w regardless of the particular system.

In matrix systems the adhesive is present in amounts ranging from 50 to 99.75% by weight and will preferably be present in amounts of between about 70 and 99.5% by weight. The enhancer is also homogeneously dissolved or suspended in the adhesive matrix and is present in amounts of between about 0.25 and 50% by weight with ranges of between about 0.5 to 30% w being preferred and 0.5 to 15% w being most preferred.

Suitable aqueous emulsion based pressure sensitive adhesives are polymeric adhesive systems in which the adhesive polymers are suspended, emulsified, or dispersed in water forming a two-phase system. Suitable aqueous emulsion based pressure sensitive adhesives may include acrylic copolymer adhesives or "acrylic adhesive", (e.g. National Starch Nacor 72-9965, Monsanto Gelva 2484, Morton Morstick 214, and Rhom and Haas Robond PS-20). Suitable acrylic adhesives may also be prepared from emulsified acrylic dispersions (e.g. BASF Acronal A217) formulated with appropriate water-compatible or water-dispersible tackifiers such as poly(vinylmethyl ethers) (e.g. BASF Lutonal M40). Suitable aqueous emulsion adhesives may also include rubber based emulsions or latexes "rubber adhesive", such as polyisobutylene or "PIB adhesive" (e.g. Lord PIB 500 or BL-100) or styrene-butadiene rubber or "SBR adhesive" (e.g. National Starch Nacor 72-8725). Rubber adhesives may also be formulated with or without water-compatible or water-dispersible tackifiers (e.g. BASF Lutonal, and Hercules Tacolyn). Suitable aqueous emulsion based pressure sensitive adhesives may also include ethylene-vinyl acetate copolymer adhesives (e.g. National Starch EVA-TACK 33-4060). However, any other suitable aqueous emulsion based pressure sensitive adhesives may also be used which are compatible with the active permeant and enhancer when utilized.

These aqueous emulsion based adhesive solutions may optionally contain thickening agents to control viscosity in amounts from 0 to 30 percent by weight. When used, thickeners are present in amounts of between about 0.1 and 30 percent with amounts of 0.1 to 20 percent being preferred. Suitable thickening agents include hydrophilic polymers such as hydroxypropyl cellulose, hydroxypropyl methylcellulose, hydroxy (ethylcellulose, ethylcellulose, carboxymethyl cellulose, dextran, gaur-gum, polyvinyl pyrrolidone, polyvinylpyrrolidone copolymers, pectins, starches, gelatin, casein, acrylic acid, acrylic acid esters, acrylic acid copolymers, polyacrylamides, polyurethanes, vinyl polymers, vinyl copolymers, vinyl alcohols, alkoxy polymers, polyethylene oxide polymers, polyethers, and the like.

Aqueous emulsion pressure sensitive adhesives may also optionally contain defoamers, wetting agents, antioxidants, preservatives, fillers, or pigments.

Additionally, glycerin may be added as an anti-irritant or to modulate the delivery of the active permeant and may be present in amounts of from 0 to 30 percent by weight. When used, glycerin is present in amounts of between about 5 and 30 percent with amounts of 10 to 20 percent being preferred.

Provided there is no negative effect on the functionality of the formulation, the drug delivery composition may, in addition, include various agents and ingredients commonly employed in dermatological preparations. Examples are, but not limited to, fragrances, pacifiers, preservatives, antioxidants, and the like.

It will be appreciated by those skilled in the art that relative amounts of the other components in these compositions can vary greatly. For example, the amount of drug present in a given composition will depend upon a variety of factors, including but not limited to, the disease or condition to be treated, the nature of the drug, the activity of the drug, the desired effect, the situs of application, possible adverse reactions, the cost and availability of the drug, solubility of the drug, and other factors within the particular knowledge of the patient and physician.

The method of application of the present invention may vary within limits, but necessarily involves applying the selected drug composition to the skin or other tissue where drug delivery is initiated and continues at a relatively sustained rate for a period of time sufficient to provide the desired pharmacological or biological response. When applied to an "application situs" for systemic delivery the method may involve the use of any suitable matrix type drug delivery device.

The matrix device is brought in contact with the skin at the application situs and is held in place on the skin at the application situs by a suitable adhesive.

It is to be understood that while the invention has been described in conjunction with the preferred specific embodiments thereof, that which follow are intended to illustrate and not limit the scope of the invention. Other aspects of the invention will be apparent to those skilled in the art to which the invention pertains.

EXPERIMENTAL

The following experiments relate to combinations of a pharmaceutically active substance and a fatty acid ester of a lactylate salt in which the transdermal permeation of the active substance is shown to be substantially increased by the presence of the fatty acid ester lactylate salt. The examples given below illustrate the transdermal permeation enhancing effect of these enhancers though it is understood that the invention will not be limited to the drug substances contained in these examples.

Adhesive Matrix Preparation

Pressure sensitive adhesive matrix systems prepared according to the following steps. First, the solids content of the adhesive solution (water or organic solvent based) was determined by placing a known weight of solution in a weighed aluminum dish and evaporating the solvents overnight in a 70° C. convection oven. The solid adhesive content of the solution was calculated by dividing the adhesive solid weight after drying by the initial total solution weight. Next, a weighed quantity of adhesive solution was added to a glass bottle and the drug substance, permeation enhancer, and other excipients were weighed and added to the adhesive solution in a quantity necessary to achieve the desired dry matrix film composition. The solution containing the adhesive polymer, drug substance, and other excipients as necessary was then mixed overnight. After mixing, approximately 8 ml of the solution was dispensed on a silanized polyester release liner and film cast using a casting knife with a gap size appropriate to achieve a final dried thickness of approximately 0.05 mm. The cast film was dried in a 70° C. convection oven until all solvents had evaporated to yield a dried matrix (15 minutes for organic solvent based adhesives, 30 minutes for water emulsion based adhesives). Finally, an 0.08 mm thick occlusive polyethylene backing film was laminated onto the dried adhesive matrix, and these systems were then used to conduct in vitro skin flux experiments as described below.

Reservoir or Free Form Hydroalcoholic Gel Preparation

Hydroalcoholic gels were prepared on a 10 ml scale as follows. Ethyl alcohol (190 proof ethanol), water, glycerin, enhancer and drug were combined in the appropriate proportions and mixed for several hours. The gelling agent (hydroxypropylcellulose) was added and the solution was mixed briefly at high shear, then mixed at low shear until a gel was formed.

Skin Flux Studies

In vitro skin flux studies were conducted using human cadaver epidermal membrane in modified Franz non-jacketed diffusion cells. The epidermal membrane (stratum corneum and epidermis) was separated from whole skin (epidermal membrane and dermis) by the method of Kligman and Christopher (*Arch. Dermatol.* 88:702 (1963)). This method involves the exposure of the full-thickness skin to water at 60° C. for a time period of 60 seconds. After this period, the epidermal membrane was gently peeled off the dermis and stored for later use in aluminum foil at -5° C.

Prior to each permeation experiment with a matrix system, the matrix system was cut into a circular sample of 0.7 cm² area and the silanized release liner was removed. The adhesive was affixed to the stratum corneum side of the thawed epidermal membrane which was then cut to an appropriate size and clamped in place between the two halves of the diffusion cell with the stratum corneum facing the donor compartment. The receiver compartment was filled with water or an aqueous solution appropriate to maintain sink conditions for the drug. All receiver solutions included 0.02% (w/w) sodium azide ($NaN_3$) to inhibit bacterial growth. The diffusion cell was placed in a temperature controlled circulating water bath calibrated to maintain the surface temperature of the skin at 32° C. The receiver compartment was constantly stirred by a magnetic stir-bar in the receiver compartment agitated by a magnetic stirring module placed under the water bath.

Permeation experiments with hydroalcoholic gels were performed using finite occluded doses. The occluded dose is an appropriate in vitro model for the application of a transdermal patch drug delivery system containing a liquid or gel reservoir.

Occluded dosing experiments were set-up according to the following procedure. Prior to skin permeation experiments, the epidermal membrane was cut to an appropriate size and placed between the two halves of the diffusion cell with the epidermal side facing the receiver compartment. The receiver compartment was filled with an appropriate solution then the diffusion cell was placed in a circulating water bath calibrated to maintain the temperature of the skin surface at 32° C. and allowed to hydrate overnight. After hydration, a sample of the gel (75 µl) was pipetted into a cavity created by placing a polyethylene washer over the stratum corneum surface. This cavity was covered with an occlusive backing film which was clamped in place.

Permeation experiments with aqueous solutions were performed using pre-saturated drug solutions containing excess drug solid (infinite dose). Prior to skin permeation experiments, the epidermal membrane was allowed to hydrate over night as described above. After hydration a well mixed sample of the aqueous solution (1 ml) was pipetted into the donor compartment formed by clamping a glass lid above the stratum corneum surface. The glass lid was then sealed with a Teflon® lined polypropylene cap.

The following sampling procedure was used for all dosage forms. At predetermined sampling time points, the entire contents of the receiver compartment were collected for drug quantitation and the receiver compartment was filled with fresh solution, taking care to eliminate any air bubbles at the skin/solution interface. The cumulative amount of drug permeated per unit area at any time $t(Q_t, \mu g/cm^2)$ was determined as follows:

$$Q_t = \sum_{N=0}^{t} (C_N * V)/A$$

where $C_N$ is the concentration (µg/ml) of the drug in the receiver sample for the corresponding sample time, V is the volume of fluid in the receiver chamber (~6.3 cm³), and A is the diffusional area of the cell (0.64 cm²).

As previously mentioned, World Patent WO 96/37231 states that acyl lactylic acids are permeation enhancers but specifically reports that the salt form is not an effective enhancer. It is generally believed in the art that salts and free acids are interconvertible in situ and therefore, if a free acid functions as an enhancer so will the salt form of that acid. In the case of fatty acid esters of lactic acid, this is been found to not be the case. The following examples demonstrate the unexpected discovery that fatty acid esters of lactic acid salts function uniquely as enhancers when formulated from aqueous emulsion based pressure sensitive adhesives as compared to fatty acid esters of lactic acid, or even formulations of fatty acid esters of lactic acid salts as aqueous solutions, hydroalcoholic gels and solvent based pressure sensitive adhesives. Therefore the combination of an acyl lactylate salt and an aqueous emulsion pressure sensitive adhesive can be shown to be an unexpectedly and unusually effective combination for transdermal drug delivery.

EXAMPLE 1

Permeation enhancement of the free acid form versus the sodium salt form of the lauroyl lactylic acid in an aqueous saturated solution was evaluated using testosterone as a model drug. The hydrogen ion concentration in these solutions was adjusted to pH 3 or pH 6 using a citric acid/phosphate buffer (CAPB). Based on the $pK_a$ of lauroyl lactylic acid ($pK_a$=4.5) it is estimated that in pH 3 CAPB more than 97% of the dissolved lauroyl lactylic acid will be in the unionized free acid form and in pH 6 CAPB more than 97% of the dissolved lauroyl lactylic acid will be in the ionized form.

Unenhanced saturated solutions of testosterone were prepared in pH 3 (Formula 1-A) and pH 6 (Formula 1-B) citric acid phosphate buffers. Enhanced formulations were prepared with 2% sodium lauroyl lactylate in pH 3 (Formula 1-C) and pH 6 (Formula 1-D) buffer solutions. Comparable enhanced formulations were prepared with lauroyl lactylic acid at pH 3 (Formula 1-E) and at pH 6 (Formula 1-F). All formulations were saturated with respect to drug and enhancer. The results of in Vitro skin permeation experiments with these solutions are summarized in Tables 1—1 and 1-2.

lauroyl lactylic acid are essentially equivalent. This is consistent with the expectations that free acids and their salt forms will show substantially the same results.

EXAMPLE 2

Permeation enhancement of the free acid form versus the sodium salt form of the lauroyl lactylic acid using testosterone as a model drug was evaluated in a hydroalcohol gel formulation. The hydrogen ion concentration in these gels was adjusted to pH 3 or pH 8 using sodium hydroxide or hydrochloric acid. Based on the lauroyl lactylic acid pKa (pKa=4.5), it is reasonable to assume that at pH 3 nearly all of the lauroyl lactylic acid will be in the unionized free acid form and at pH 8 nearly all of the lauroyl lactylic acid will be in the ionized form. Unenhanced solutions of testosterone (15 mg/ml) were prepared in pH 3 (Formula 2-A) and pH 8 (Formula 2-B) solutions of EtOH/H2O in the proportions of 65/35% (v/v). Enhanced formulations were prepared with

TABLE 1-1

| Skin Source | Formula 1-A Unenhanced pH3 | Formula 1-C 2% Na Lauroyl Lactylate Unionized[a] pH3 | | Formula 1-B Unenhanced pH6 | Formula 1-D 2% Na Lauroyl Lactylate Ionized[b] pH6 | |
|---|---|---|---|---|---|---|
| | Q24 | Q24 | E | Q24 | Q24 | E |
| 1-I | 6.9 ± 4.8 (n =5) | 15.7 ± 1.9 (n=5) | 2.3 (n=5) | 7.6 ± 0.6 (n=5) | 21.7 ± 1.6 | 2.9 |
| 1-II | 9.6 ± 4.1 (n=5) | 16.5 ± 3.5 (n=5) | 1.7 (n=5) | 8.2 ± 3.1 (n=5) | 30.9 ± 8.7 | 3.7 |
| 1-III | 18.7 ± 5.2 (n=5) | 22.4 ± 3.8 (n=5) | 1.2 (n=5) | 19.0 ± 8.2 (n=5) | 47.3 ± 2.5 | 2.5 |
| All Skins | 11.7 ± 8.2 | 18.2 ± 3.7 | 1.7 ± 0.5 | 11.6 ± 6.4 | 33.3 ± 13.0 | 3.0 ± 0.6 |

[a]At this pH >97% of lauroyl lactylic acid should be present in the unionized free acid form.
[b]At this pH >97% of lauroyl lactylic acid is present in the ionized salt form.

TABLE 1-2

| Skin Source | Formula 1-A Unenhanced pH3 | Formula 1-E 2% Na Lauroyl Lactylate Unionized[a] pH3 | | Formula 1-B Unenhanced pH6 | Formula 1-F 2% Na Lauroyl Lactylate Ionized[b] pH6 | |
|---|---|---|---|---|---|---|
| | Q24 | Q24 | E | Q24 | Q24 | E |
| 1-IV | 4.6 ± 0.5 (n=5) | 9.9 ± 1.1 (n=5) | 2.2 (n=5) | 4.7 ± 0.9 (n=4) | 17.7 ± 0.3 | 3.7 |
| 1-V | 6.5 ± 1.3 (n=4) | 9.7 ± 1.3 (n=5) | 1.5 (n=5) | 5.9 ± 1.8 (n=5) | 22.0 ± 3.1 | 3.7 |
| 1-VI | 18.0 ± 6.9 (n=3) | 27.2 ± 9.2 (n=4) | 1.5 (n=5) | 18.0 ± 2.7 (n=4) | 33.1 ± 7.0 | 1.8 |
| All Skins | 9.7 ± 7.3 | 15.6 ± 10.0 | 1.7 ± 0.4 | 9.5 ± 7.4 | 24.3 ± 7.9 | 3.1 ± 1.1 |

[a]At this pH >97% of lauroyl lactylic acid should be present in the unionized free acid form.
[b]At this pH >97% of lauroyl lactylic acid is present in the ionized salt form.

The control formulations show that testosterone permeation in the unenhanced formulations is not significantly affected by the pH of the aqueous buffer. Both the free acid and the salt form of lauroyl lactylic acid show significant permeation enhancement and the permeation enhancement of the ionized form (at pH 6) is greater than that of the unionized form (at pH 3). Approximately the same permeation enhancement is observed whether the starting material is the salt or the free acid indicating that when added to an aqueous solution at a fixed pH the salt and free base form of 2% (w/v) sodium lauroyl lactylate in pH 3 (Formula 2-C) and pH 8 (Formula 2-D) solutions. Comparable enhanced formulations were prepared with 2% (w/v) lauroyl lactylic acid in pH 3 (Formula 2-E) and in pH 8 (Formula 2-F). Each solution was gelled with 3% (w/v) hydroxypropylcellulose (Klucel HF) The drug and enhancer were fully dissolved in all formulations. The results of in vitro skin permeation experiments with these gels are summarized in Tables 2-1 and 2—2.

TABLE 2-1

| Skin Source | Formula 2-A Unenhanced pH3 | Formula 2-C 2% Na Lauroyl Lactylate Unionized[a] pH3 | | Formula 2-B Unenhanced pH8 | Formula 2-D 2% Na Lauroyl Lactylate Ionized[b] pH8 | |
|---|---|---|---|---|---|---|
| | Q24 | Q24 | E | Q24 | Q24 | E |
| 2-I | 129.1 ± 29.1 (n=5) | 287.7 ± 43.5 (n=5) | 2.2 (n=5) | 118.5 ± 30.6 (n=5) | 149.0 ± 42.0 | 1.3 |
| 2-II | 150.8 ± 21.1 (n=5) | 372.3 ± 28.5 (n=5) | 2.5 (n=5) | 141.9 ± 20.0 (n=5) | 195.6 ± 13.3 | 1.4 |
| All Skins | 140.0 ± 15.3 | 330.0 ± 59.8 | 2.4 ± 0.2 | 130.0 ± 16.6 | 172.3 ± 33.0 | 1.4 ± 0.1 |

[a]At this pH >97% of lauroyl lactylic acid should be present in the unionized free acid form.
[b]At this pH >97% of lauroyl lactylic acid is present in the ionized salt form.

TABLE 2-2

| Skin Source | Formula 2-A Unenhanced pH3 | Formula 2-E 2% Na Lauroyl Lactylate Unionized[a] pH3 | | Formula 2-B Unenhanced pH8 | Formula 2-F 2% Na Lauroyl Lactylate Ionized[b] pH8 | |
|---|---|---|---|---|---|---|
| | Q24 | Q24 | E | Q24 | Q24 | E |
| 2-I | 87.9 ± 22.1 (n=5) | 173.4 ± 38.6 (n=5) | 2.0 (n=5) | 56.4 ± 15.4 (n=5) | 113.5 ± 15.0 | 2.0 |
| 2-II | 191.3 ± 56.1 (n=5) | 525.3 ± 74.9 (n=5) | 2.8 (n=4) | 179.8 ± 46.0 (n=5) | 237.1 ± 40.3 | 1.3 |
| All Skins | 139.6 ± 73.1 | 349.4 ± 248.8 | 2.4 ± 0.6 | 118.1 ± 87.3 | 175.3 ± 87.4 | 1.7 ± 0.5 |

[a]At this pH >97% of lauroyl lactylic acid should be present in the unionized free acid form.
[b]At this pH >97% of lauroyl lactylic acid is present in the ionized salt form.

The unenhanced control formulations show that testosterone permeation in the unenhanced formulations is not significantly affected by the pH of the gel.

Both the free acid and the sodium salt form of lauroyl lactylic acid show significant permeation enhancement and the permeation enhancement of the unionized form (at pH 3) is greater than that of the ionized form (at pH 8). Approximately the same permeation enhancement is observed whether the starting material is the lauroyl lactylic acid salt or the free acid indicating that when added to a hydroalcoholic gel system at a fixed pH the salt and free acid form of lauroyl lactylic acid are virtually equivalent. This result is consistent with what might be predicted based on the interchangeability of free acids and salts.

EXAMPLE 3

Permeation enhancement of the free acid form versus the sodium salt form of the lauroyl lactylic acid in a organic solvent based pressure sensitive adhesive was evaluated using estradiol as a model drug. An appropriate amount of estradiol was incorporated in a pressure sensitive adhesive (National Starch 2516) to achieve a dried adhesive/estradiol composition of 98.5/1.5% (w/w) (Formula 3-A). Comparable formulations of 1.5% estradiol and 96.5% adhesive were prepared with 2.0% lauroyl lactylic acid (Formula 3-B) or 2.0% sodium lauroyl lactylate (Formula 3-C). The drug and enhancer were fully dissolved in all formulations. The results of in vitro skin permeation experiments using these dried adhesive matrices are shown in Table 3-1.

TABLE 3-1

| Skin Source | Formula 3-A Unenhanced | Formula 3-B 2% Lauroyl Lactylic Acid | | Formula 3-C 2% Na Lauroyl Lactylate | |
|---|---|---|---|---|---|
| | Q24 | Q24 | E | Q24 | E |
| 3-I | 5.0 ± 1.0 (n=4) | 7.9 ± 1.9 (n=4) | 1.6 | 5.4 ± 0.9 (n=4) | 1.1 |
| 3-II | 4.7 ± 0.7 (n=4) | 10.0 ± 1.6 (n=4) | 2.1 | 6.5 ± 0.8 (n=4) | 1.4 |

TABLE 3-1-continued

| Skin Source | Formula 3-A Unenhanced Q24 | Formula 3-B 2% Lauroyl Lactylic Acid | | Formula 3-C 2% Na Lauroyl Lactylate | |
|---|---|---|---|---|---|
| | | Q24 | E | Q24 | E |
| 3-III | 5.0 ± 1.1 (n=4) | 7.2 ± 1.1 (n=4) | 1.5 | 8.2 ± 0.B (n=4) | 1.6 |
| All Skins | 4.9 ± 0.2 | 8.4 ± 1.5 | 1.7 ± 0.4 | 6.7 ± 1.4 | 1.4 ± 0.3 |

These results show the sodium salt form of lauroyl lactylic acid is less effective as a permeation enhancer than the free acid form when used with buspirone free base in an organic solvent based acrylic pressure sensitive adhesive.

EXAMPLE 4

Permeation enhancement of the potassium salt form of lauroyl lactylic acid (R.I.T.A. Corp., Woodstock, Ill.) in an aqueous emulsion based acrylic pressure sensitive adhesive (PSA) was evaluated using buspirone HCl as a model drug. An appropriate amount of Buspirone HCl was incorporated in an aqueous emulsion based adhesive (Nacor 72-9965) to achieve a dried adhesive/drug composition of 95/5% (w/w) (Formula 4-A). A Comparable formulation of 5% buspirone and 93% adhesive was prepared with 2% potassium lauroyl lactylate (Formula 4-B). The drug and enhancer were fully dissolved in all formulations. The results of in vitro skin permeation experiments using these dried adhesive matrices are shown in Table 4-1.

TABLE 4-1

| Skin Source | Formula 4-A Unenhanced Q24 | Formula 4-B 2% K Lauroyl Lactylate | |
|---|---|---|---|
| | | Q24 | E |
| 4-I | 94.3 ± 18.8 (n=5) | 149.8 ± 23.9 (n=5) | 1.6 |
| 4-II | 57.8 ± 8.2 (n=5) | 98.1 ± 25.7 (n=5) | 1.7 |
| 4-III | 93.0 ± 8.4 (n=5) | 148.7 ± 17.1 (n=5) | 1.8 |
| All Skins | 81.7 ± 20.7 | 132.2 ± 29.5 | 16 ± 0.1 |

These results show the potassium salt form, potassium lauroyl lactylate, is also an unexpectedly effective permeation enhancer, when formulated in an emulsion based pressure sensitive adhesive.

EXAMPLE 5

Permeation enhancement of the potassium salt form of lauroyl lactylic acid using buspirone free base as a model drug was evaluated in an organic solvent based acrylic pressure sensitive adhesive. An appropriate amount of buspirone was incorporated in an organic solvent based adhesive (Duro-tak 2516) to achieve a dried adhesive/drug composition of 98/2% (w/w) (Formula 5-A). Comparable formulations of 2% buspirone and 96% adhesive were prepared with 2% potassium lauroyl lactylate (Formula 5-B). The drug and enhancer were fully dissolved in all formulations. The results of in vitro skin permeation experiments using these systems are shown in Table 5-1.

TABLE 5-1

| Skin Source | Formula 5-A Unenhanced Q24 | Formula 5-B 2% K Lauroyl Lactylate | |
|---|---|---|---|
| | | Q24 | E |
| 5-I | 138.1 ± 7.9 (n=5) | 117.8 ± 8.2 (n=5) | 0.9 |
| 5-II | 107.1 ± 14.2 (n=5) | 88.0 ± 14.7 (n=5) | 0.8 |
| 5-III | 62.4 ± 6.8 (n=5) | 51.7 ± 7.0 (n=5) | 0.8 |
| All Skins | 102.5 ± 38.1 | 85.8 ± 33.7 | 0.8 ± 0.1 |

These results show the potassium salt form is not an effective permeation enhancers when used in combination with an organic solvent based acrylic pressure sensitive adhesive. This contrasts with the results observed in Example 4 in which the potassium salt form of lauroyl lactylic acid is shown to be an unexpectedly effective permeation enhancer when used with an aqueous emulsion pressure sensitive adhesive.

EXAMPLE 6

Sodium salts of fatty acid lactylates of various fatty acid chain lengths were evaluated using buspirone HCl as a model compound. An aqueous emulsion based pressures sensitive acrylic copolymer adhesive (Nacor 72-9965, National Starch and Chemical, New Jersey) was used with buspirone HCl to prepare an unenhanced formulation at a concentration of 2% (w/w) (Formulation 6-A). The fatty acid lactylate salts were all obtained from R.I.T.A. Corporation (Woodstock, Ill.) and included a C12 (Sodium Lauroyl Lactylate, Pationic 138C), a C10 (Sodium Caproyl Lactylate, Pationic 122A), and a mixture of $C_{12}$–C18 fatty acids derived from coconut oil (Sodium Cocoyl Lact-ylate, Pationic SCL). The results of in vitro skin permeation experiments using these fatty acid lactylate salts at 2.5% (w/w) (Formulations 6-B,C, and D) are shown in Table 6-1.

TABLE 6-1

| Skin Source | Formula 6-A 98/2% Q24 | Formula 6-B Na Lauroyl ($C_{12}$) Lactylate 95.5/2/2.5% (w/w) Q24 | E | Formula E-C Na Caproyl ($C_{10}$) Lactylate 905/2/2.5% (w/w) Q24 | E | Formula 6-D Na Cocoyl ($C_{12}$-$C_{10}$) * Lactylate 9.5/2/2.5% Q24 | E |
|---|---|---|---|---|---|---|---|
| 6-I | 18 ± 12 (n=5) | 36 ± 18 (n=5) | 1.9 | 31 ± 15 (n=5) | 1.7 (n=5) | 38 ± 16 | 2.1 |
| 6-II | 9.5 ± 5 (n=5) | 21 ± 3 (n=5) | 2.2 | 16 ± 3 (n=5) | 1.7 (n=5) | 13 ± 2.4 | 1.4 |
| All Skins (Means) | 14 ± 10 (n=10) | 29 ± 14 (n=10) | 2.1 ± 0.2 | 23 ± 13 (n=10) | 1.7 ± 0.04 | 26 ± 17 (n=10) | 1.7 ± 5 |

*Fatty acids derived from coconut oil, mixture of $C_{14}$, $C_{12}$, $C_{18}$ and others.

As shown in Table 6-1, all fatty acid lactylate salts tested effectively increased the permeation of buspirone from the matrix system. The most effective enhancement was observed with the lauric acid derivative (Formula 6-B) suggesting that the $C_{12}$ fatty acid chain length may be the preferred fatty acid lactylate for use as a permeation enhancer.

EXAMPLE 7

Permeation enhancement by a fatty acid lactylate salt was also evaluated with the basic antihypertensive drug clonidine in both free base and HCl acid addition salt forms. Matrix systems were prepared with (a) 2% (w/w) clonidine HCl in 98% (w/w) of an aqueous emulsion based acrylic copolymer adhesive (Nacor 72-9965, National Starch and Chemical Company, New Jersey) (Formula 7-A), and (b) 2% (w/w) clonidine HCl in 98% (w/w) of an aqueous emulsion based ethylene-vinyl acetate copolymer adhesive (EVA-TAK 33-4060, National Starch and Chemical Company, New Jersey) (Formula 7-C), (c) an aqueous emulsion based polyisobutylene and butyl latex blended adhesive (33% BL-100, 65% PIB-500, Lord Corporation, Pompano Beach, Fla.) (Formula 4-7) and (d) 1.7% (w/w) clonidine free base in 98.3% (w/w) of an organic solvent based acrylic copolymer adhesive (Duro-Tak 2516, National Starch and Chemical Company, Bridgewater, N.J.) (Formula 7-G). Enhanced formulations were prepared for comparison by adding 2.5% (w/w) of sodium lauroyl lactylate (Pationic 138C, R.I.T.A. Corporation, Woodstock, Ill.) as an enhancer and reducing the adhesive to compensate. (Formulas 7-B, 7-D, 7-F and 7-H respectively). The drug and enhancer were fully dissolved in all formulations. The results of the in vitro skin permeation for the unenhanced and enhanced systems are shown in Tables 7-1, 7-2, 7-3 and 7-4.

TABLE 7-1

(Clonidine HCl in Nacor 72-9965 Adhesive)

| Skin Source | Formula 7-A 98/2% (w/w) Q24 | Formula 7-B Sodium Lauroyl Lactylate 95.5/2/2.5% (w/w) Q24 | E |
|---|---|---|---|
| 7-I | 12.2 ± 3.2 (n=5) | 31.8 ± 1.3 (n=5) | 2.6 |
| 7-II | 5.7 ± 2.6 (n=5) | 9.9 ± 3.1 (n=5) | 1.7 |
| 7-III | 9.1 ± 2.8 (n=4) | 16.2 ± 8.5 (n=5) | 1.8 |
| 7-IV | 7.1 ± 4.2 (n=5) | 16.7 ± 6.4 (n=5) | 2.3 |
| All Skins | 8.5 ± 3.9 (n=19) | 18.7 ± 9.7 (n=20) | 2.1 ± 0.4 |

TABLE 7-2

(Clonidine HCl in EVA-TAK 33-4060)

| Skin Source | Formula 7-C 98/2% (w/w) Q24 | Formula 7-D Sodium Lauroyl Lactylate 95.5/2/2.5% (w/w) Q24 | E |
|---|---|---|---|
| 7-V | 36.7 ± 16.8 (n=5) | 123.5 ± 32.9 (n=5) | 3.4 |
| 7-VI | 8.2 ± 5.9 (n=5) | 20.5 ± 7.1 (n=5) | 2.5 |
| 7-VII | 9.2 ± 1.5 (n=3) | 13.2 ± 2.4 (n=5) | 1.4 |
| All Skins | 19.4 ± 17.6 (n=13) | 52.4 ± 55.1 (n=15) | 2.4 ± 1.0 |

TABLE 7-3

(Clonidine HCl in PIB/Butyl Latex Adhesive)

| Skin Source | Formula 7-E 33/65/2% (w/w) Q24 | Formula 7-F Sodium Lauroyl Lactylate 32/63.5/2/2.5% (w/w) Q24 | E |
|---|---|---|---|
| 7-VIII | 13.2 ± 6.1 (n=5) | 23.2 ± 5.9 (n=5) | 1.8 |
| 7-IX | 7.2 ± 0.9 (n=4) | 17.0 ± 2.3 (n=4) | 2.4 |

TABLE 7-3-continued (Clonidine HC1 in PIB/Butyl Latex Adhesive)

| Skin Source | Formula 7-E 33/65/2% (w/w) Q24 | Formula 7-F Sodium Lauroyl Lactylate 32/63.5/2/2.5% (w/w) Q24 | E |
|---|---|---|---|
| All Skins | 10.5 ± 5.3 (n=9) | 20.5 ± 5.5 (n=9) | 2.1 ± 0.4 |

TABLE 7-4

(Clonidine Base in Duro-Tak 97-2516 Adhesive)

| Skin Source | Formula 7-G 98.3/1.7% (w/w) Q24 | Formula 7-H Sodium Lauroyl Lactylate 95.8/1.7/2.5% (w/w) Q24 | E |
|---|---|---|---|
| 7-X | 37.0 ± 5.1 (n=5) | 43.8 ± 4.9 (n=5) | 1.18 |
| 7-XI | 65.2 ± 27.5 (n=5) | 49.9 ± 5.5 (n=5) | 0.77 |
| All Skins | 51.1 ± 23.9 (n=10) | 46.8 ± 5.9 (n=10) | 0.92 ± 0.29 |

As demonstrated in Tables 7-1, 7-2 and 7-3, sodium lauroyl lactylate was a consistently effective enhancer in all of the aqueous emulsion based matrix systems tested, increasing the permeation of clonidine about two fold over its unenhanced counterpart. As shown in Table 7-4, sodium lauroyl lactylate was not an effective enhancer in the organic solvent based adhesive matrix. These results provide evidence that fatty acid lactylate salts are effective permeation enhancers in a variety of aqueous emulsion based adhesive matrix types and further illustrates that this permeation enhancement with the fatty acid lactylate salts is not observed in an organic solvent based acrylic adhesive matrix.

EXAMPLE 8

The effect of fatty acid lactylate salts on the permeation of a model acidic drug from some copolymer adhesive matrix systems was evaluated using diclofenac, a non-steroidal anti-inflammatory. The following matrix systems were prepared to test the effect of fatty acid lactylate salts on the permeation of this acidic compound from copolymer adhesives: (a) Diclofenac acid at 1.8% (w/w) in Durotak 87-2516 (National Starch and Chemical, New Jersey), a solvent based acrylic adhesive, at 92.8% (w/w) (Formula 8-A); (b) sodium diclofenac at 2.0% (w/w) in Nacor 72-9965 (National Starch and Chemical Company, New Jersey), an aqueous emulsion based acrylic adhesive, at 98% (w/w) (Formula 8-C); sodium diclofenac at 2.0% (w/w) and Robond PS-20 (Rohm and Haas, Philadelphia, Pa.) an aqueous emulsion based acrylic adhesive, at 93.6% (w/w) with polyvinylpyrrolidone (PVP, Kollidon 90, BASF, New Jersey) at 2.0% (w/w) as a thickening agent (Formula 8-E). Enhanced formulations were prepared for comparison by adding 2.5% (w/w) of sodium lauroyl lactylate (Pationic 138C) as an enhancer and reducing the adhesive concentration to compensate (Formulas 8-B, 8-D and 8-F respectively). Results of in vitro skin permeation for the unenhanced and enhanced systems are shown in Tables 8-1, 8-2 and 8-3.

TABLE 8-1

(Diclofenac Acid in Durotak 87-2516 Adhesive)

| Skin Source | Formula 8-A 98.2/1.8% (w/w) Q24 | Formula 8-B Sodium Lauroyl Lactylate 95.7/1.8/2.5% (w/w) Q24 | E |
|---|---|---|---|
| 8-I | 30.23 ± 3.49 (n=5) | 38.69 ± 3.89 (n=5) | 1.3 |
| 8-II | 4.13 ± 0.71 (n=5) | 6.78 ± 1.55 (n=5) | 1.6 |
| All Skins (mean) | 17.18 ± 13.96 (n=10) | 22.73 ± 17.05 (n=10) | 1.5 ± 0.3 |

TABLE 8-2

(Sodium Diclofenac in Nacor 72-9965 Adhesive)

| Skin Source | Formula 8-C 98/2% (w/w) Q24 | Formula 8-D Sodium Lauroyl Lactylate 95.5/2/2.5% (w/w) Q24 | E |
|---|---|---|---|
| 8-III | 20.73 ± 1.72 (n=5) | 27.39 ± 4.26 (n=5) | 1.32 |
| 8-IV | 2.13 ± 0.44 (n=5) | 3.39 ± 1.15 (n=5) | 1.59 |
| All Skins (mean) | 11.43 ± 9.87 (n=10) | 15.39 ± 12.98 (n=10) | 1.45 ± 0.2 |

TABLE 8-3

(Sodium Diclofenac in Robond PB-20 Adhesive)

| Skin Source | Formula 8-E 96/2/2% (w/w) Q24 | Formula 8-F Sodium Lauroyl Lactylate 93.5/2/2.0/2.5% (w/w) Q24 | E |
|---|---|---|---|
| 8-V | 28.1 ± 5.4 (n=5) | 36.8 ± 8.5 (n=5) | 1.3 |
| 8-VI | 14.3 ± 6.4 (n=5) | 19.8 ± 6.3 (n=5) | 1.4 |
| 8-VII | 22.2 ± 3.8 (n=5) | 30.5 ± 4.5 (n=5) | 1.4 |
| All Skins (mean) | 21.5 ± 7.6 (n=15) | 29.0 ± 9.5 (n=15) | 1.36 ± 0.04 |

Sodium lauroyl lactylate was a consistently effective enhancer in all of the matrix systems tested. The permeation with the system containing the acid form of diclofenac was increased about 50% by the addition of 2.5% sodium lauroyl lactylate as shown in Table 8-1, and the permeation with systems prepared from the sodium salt of diclofenac was increased by 36 to 45% in the two adhesives tested as demonstrated in Tables 8-2 and 8-3. These results illustrate that fatty acid lactylate salts are also effective permeation enhancers for acidic substances. While Formulas 8-A and 8-B utilize a solvent based adhesive and show enhancement comparable to the aqueous emulsion based adhesive formulations of Formulas 8-C through 8-F, a comparison of Formula 8-B with a formula containing lauroyl lactylate as a free acid instead of the salt form will show somewhat comparable results. On the other hand, a comparison of Formulas 8-D and 8-F with formulas containing lauroyl lactylate as a free acid instead of the salt form will show significant reduction in enhancement when using the free acid form.

The above examples are but illustrative of drugs or transdermal formulations which may be employed in operation of the present invention. The invention is directed to the discovery that the utilization of matrix patches formed from aqueous based emulsions of pressure sensitive adhesives and fatty acid esters of lactic acid salts as defined above enhances the cumulative amount of drug delivered as compared to fatty acid esters of lactic acid, formulations of lactic acid salts with solvent based adhesives, formulation of lactic acid salts with hydroalcoholic gels, and the like. While the certain fatty acids and lactic acid salts have been primarily used for purposes of illustration other aliphatic esters of lactic acid salts may also be utilized and similar results will be realized. Therefore, specific drugs and/or formulations are not critical as long as they are compatible with the fatty acid esters of lactic acid salts as disclosed herein. Within the guidelines presented herein, a certain amount of experimentation to obtain optimal formulations can be readily carried out by those skilled in the art. Therefore, the invention is limited in scope only by the following claims and functional equivalents thereof.

We claim:

1. A pharmaceutical composition for transdermal application having penetration-enhancing properties comprising:
   (a) a safe and effective amount of an active pharmaceutical permeant contained in,
   (b) a penetration-enhancing system comprising,
      (i) about 0.25 to about 50% by weight of an enhancer consisting of the fatty acid esters of lactic acid salts represented by the formula:

$$[RCO-(O-CH(CH_3)-CO)_aO]_bM$$

where R is a $C_5$ to $C_{21}$ alkyl or alkenyl group which may be either straight or branched chained and which may contain hydroxy substituents; a is an integer of 1 to 4, b is 1 or 2 and M is a pharmaceutically acceptable salt forming counterion having a valency of 1 or 2; and
      (ii) a pharmaceutically suitable pressure sensitive adhesive carrier vehicle formed from an aqueous based emulsion.

2. A composition according to claim 1 wherein the active permeant and enhancer are homogeneously contained in said carrier vehicle.

3. A composition according to claim 2 wherein M is a salt forming counterion selected from the group consisting of Na, K, Ca, Mg and ammonium or amines salts.

4. A composition according to claim 3 wherein the enhancer is present in the penetration enhancing system in an amount ranging from 0.25 to 30% by weight.

5. A composition according to claim 4 wherein the pressure sensitive adhesive is a member selected from the group consisting of acrylic, rubber and ethylene-vinyl acetate adhesives.

6. A composition according to claim 5 in the form of a matrix system having an occlusive backing.

7. A composition according to claim 6 wherein the enhancer is sodium lauroyl lactylate.

8. A composition according to claim 6 wherein the enhancer is potassium lauroyl lactylate.

9. A composition according to claim 5 wherein the adhesive is an acrylic adhesive.

10. A composition according to claim 5 wherein the adhesive is an ethylene-vinyl acetate adhesive.

11. A method for enhancing the penetration of an active pharmaceutical permeant through the skin of a human or warm-blooded animal which comprises applying to the skin a composition comprising:
    (a) a safe and effective amount of an active pharmaceutical permeant contained in,
    (b) a penetration-enhancing system comprising,
       (i) about 0.25 to about 50% by weight of an enhancer consisting of the fatty acid esters of lactic acid salts represented by the formula:

$$[RCO-(O-CH(CH_3)-CO)_aO]_bM$$

where R is a $C_5$ to $C_{21}$ alkyl or alkenyl group which may be either straight or branched chained and which may contain hydroxy substituents; a is an integer of 1 to 4, b is 1 or 2 and M is a pharmaceutically acceptable salt forming counterion having a valency of 1 or 2; and
       (ii) a pharmaceutically suitable pressure sensitive adhesive carrier vehicle formed from an aqueous based emulsion.

12. A method according to claim 11 wherein the active permeant and enhancer are homogeneously contained in said carrier vehicle.

13. A method according to claim 12 wherein M is a salt forming counterion selected from the group consisting of Na, K, Ca, Mg and ammonium or amines salts.

14. A method according to claim 13 wherein the enhancer is present in the penetration enhancing system in an amount ranging from 0.25 to 30% by weight.

15. A method according to claim 14 wherein the pressure sensitive adhesive is a member selected from the group consisting of acrylic, rubber and ethylene-vinyl acetate adhesives.

16. A method according to claim 15 wherein the composition is applied to an application situs in the form of a matrix system having an occlusive backing.

17. A method according to claim 16 wherein the enhancer is sodium lauroyl lactylate.

18. A method according to claim 16 wherein the enhancer is potassium lauroyl lactylate.

19. A method according to claim 15 wherein the adhesive is an acrylic adhesive.

20. A method according to claim 19 wherein the adhesive is an ethylene-vinyl acetate adhesive.

* * * * *